(12) United States Patent  
Moriyama et al.

(10) Patent No.: US 7,048,898 B1  
(45) Date of Patent: May 23, 2006

(54) APPARATUS FOR PREPARING A FLUID FOR A MEDICAL PROCEDURE

(75) Inventors: Naohiko Moriyama, Tokyo (JP); Tetsuya Yano, Hino (JP); Ken Imai, Hino (JP); Tsuneo Deguchi, Hino (JP)

(73) Assignees: Teijin Linited, Osaka (JP); Aksys Ltd., Lincolnshire, IL (US)

( * ) Notice: Subject to any disclaimer, the term of this patent is extended or adjusted under 35 U.S.C. 154(b) by 0 days.

(21) Appl. No.: 09/868,580

(22) PCT Filed: Dec. 21, 1999

(86) PCT No.: PCT/JP99/07165

§ 371 (c)(1),  
(2), (4) Date: Jun. 20, 2001

(87) PCT Pub. No.: WO00/37127

PCT Pub. Date: Jun. 29, 2000

(30) Foreign Application Priority Data

Dec. 21, 1998 (JP) ................................. 10-362828

(51) Int. Cl.
- *B01D 11/02* (2006.01)
- *B67D 5/00* (2006.01)
- *B01F 15/00* (2006.01)
- *B65D 25/08* (2006.01)
- *B26D 1/02* (2006.01)

(52) U.S. Cl. ................... 422/261; 422/63; 422/104; 422/252; 422/263; 422/266; 422/268; 422/269; 137/68.29; 222/5; 222/541.2; 366/167.1; 366/183.1; 206/219; 206/222; 206/568; 206/80; 206/81; 206/83.5; 206/630; 83/505; 83/509; 83/515; 83/667; 83/669; 83/682

(58) Field of Classification Search ............. 137/68.29; 222/5, 541.2; 366/167.1, 183.1; 206/219, 206/222, 568, 80, 81–83, 83.5, 88, 630, 637; 422/63, 104, 252–256, 261, 263–264, 266, 422/268–269; 83/505, 509, 515, 667, 669, 83/682

See application file for complete search history.

(56) References Cited

U.S. PATENT DOCUMENTS 3,168,379 A 2/1965 Miller et al.

(Continued)

FOREIGN PATENT DOCUMENTS

JP 59-142890 A 8/1984

(Continued)

OTHER PUBLICATIONS

Japanese Office Action dated Aug. 24, 2004, 2 pages.

(Continued)

*Primary Examiner*—Richard Crispino  
*Assistant Examiner*—Monzer R. Chorbaji

(57) ABSTRACT

The invention provides an apparatus for preparing a fluid for a medical procedure by mixing of at least one medicament in the form of powder with water, the medicament is held in a vessel which defines a bottom, a side wall, and a top opening which is closed by an membrane for sealing the inside of the vessel. The apparatus includes an opener for opening the membrane of the vessel. The opener includes a holder for vertically holding the vessel to downwardly orient the opening; a cutter, provided beneath the opening of the vessel held by the holder, for partially cutting the membrane along the periphery of the opening; a mechanism for vertically moving the holder toward the cutter so that the cutting edge of the cutter pierces to partially separate the membrane from the periphery of the opening whereby the medicament in the vessel falls from the vessel; a receiving member, in the form of a mesh provided beneath the cutter, for receiving all of the medicament from the vessel; and a nozzle for directing water from the source of water in the form of a spray to the medicament received by the receiving member to dissolve the medicament into the water directed to the medicament.

14 Claims, 13 Drawing Sheets

U.S. PATENT DOCUMENTS

| | | | | |
|---|---|---|---|---|
| 3,581,605 A | * | 6/1971 | Taylor | 81/3.49 |
| 4,026,673 A | | 5/1977 | Russo | |
| 4,197,942 A | * | 4/1980 | Gacki et al. | 206/219 |
| 5,366,114 A | * | 11/1994 | Bernstein et al. | 222/83 |
| 5,547,645 A | | 8/1996 | Ego et al. | 422/264 |
| 5,788,099 A | * | 8/1998 | Treu et al. | 215/230 |
| 6,210,646 B1 | * | 4/2001 | Larson et al. | 422/261 |

FOREIGN PATENT DOCUMENTS

| | | |
|---|---|---|
| JP | 60-058231 A | 4/1985 |
| JP | 63-154034 U | 10/1988 |
| JP | 01-104261 A | 4/1989 |
| JP | 4-84967 | 3/1992 |
| JP | 5-168678 | 7/1993 |
| JP | 09-226848 A | 9/1997 |

OTHER PUBLICATIONS

Japanese Office Action mailed on Apr. 26, 2005.

* cited by examiner

APPARATUS FOR PREPARING A FLUID FOR A MEDICAL PROCEDURE

BACKGROUND OF THE INVENTION

1. Field of the Invention

The invention relates to an apparatus for preparing a fluid for a medical procedure, an opener for unsealing a vessel containing a medicament, and a cutter for the opener.

2. Description of the Related Art

Recently, an apparatus for preparing a fluid for a medical procedure, such as dialysis treatment, has been proposed. The fluids for dialysis treatment includes an acetic acid aqueous solution, which is prepared by diluting an acetic acid stock solution with water, in particular reverse osmosis water (referred to RO water in this specification), and a sodium bicarbonate aqueous solution, which is prepared by dissolving sodium bicarbonate powder in RO water.

Japanese Patent Publication (Kokai) No. 5-168678 (JPP '678) describes an apparatus for preparing sodium bicarbona aqueous solution. The apparatus holds an inverted vessel for containing a solid medicament, sodium bicarbona, in the form of a powder or granules, after the vessel is unsealed, so that the contents fall by gravity into a tank which contains water. The tank includes an agitator for promoting the mixing of the medicament with the water. The apparatus of JPP '678 has a problem that the sodium bicarbona, which has been fallen into the tank, cannot be solved quickly in the water within the tank since the dissolid medicament deposits on the bottom of the tank.

Japanese Patent Publication (Kokai) No. 4-84967 (JPP '967) also describes an apparatus for preparing sodium bicarbona aqueous solution. The apparatus is configured to dissolve and wash out sodium bicarbonate contained within a vessel by spraying water into the inverted vessel after the vessel is unsealed. However, with the apparatus of JPP '967, dissolving the solid content within the vessel cannot be sufficiently carried out due the small volume available for the dissolving process so that the substantial portion of the sodium bicarbona is wash out of the vessel without dissolving into the water sprayed into the vessel.

SUMMARY OF THE INVENTION

The invention is directed to solve the prior art problems, and to provide an improved apparatus for preparing a fluid for a medical procedure.

Further, the objective of the invention is to provide an opener for unsealing a vessel containing a medicament used for preparing the fluid for a medical procedure Further, the objective of the invention is to provide a cutter for the opener.

The invention provides an apparatus for preparing a fluid for a medical procedure by mixing of at least one medicament in the form of powder with water, the medicament is held in a vessel which defines a bottom, a side wall, and a top opening which is closed by an membrane for sealing the inside of the vessel. The apparatus includes a source of water for dissolving the medicament. An opener is provided for opening the membrane of the vessel. The opener includes a holder for vertically holding the vessel to downwardly orient the opening; a cutter, provided beneath the opening of the vessel held by the holder, for partially cutting the membrane along the periphery of the opening; a mechanism for vertically moving the holder toward the cutter so that the cutting edge of the cutter pierces to partially separate the membrane from the periphery of the opening whereby the medicament in the vessel falls from the vessel; a receiving member, in the form of a mesh provided beneath the cutter, for receiving all of the medicament from the vessel; and a nozzle for directing water from the source of water in the form of a spray to the medicament received by the receiving member to dissolve the medicament into the water directed onto the medicament. A tank is provided for receiving and containing the substances dissolved into the sprayed water.

According to one feature of the invention, the tank is adapted to receive the water from the water source. The apparatus further includes a circulating system for supplying the water from the tank to the nozzle.

According to another feature of the invention, the opener may include a housing for enclosing the cutter and the receiving member. The holder is vertically displaceable relative to the housing; and the nozzle is attached to the housing to direct the water to the medicament received by the receiving member from outside of the housing.

According to another feature of the invention, the mechanism includes a feed screw vertically supported for rotation; a motor, connected to one end of the feed screw, for rotating the screw; a nut engaging the feed screw; and a member connected between the nut and the holder.

According to another feature of the invention, the cutting edge includes a serrated portion provided along the inclined end. The serrated portion may be partially provided along the inclined end of the cutter body and, in particular, disposed on the proximal half of the inclined end. The serrated portion may be provided all around the inclined end of the cutter body.

DESCRIPTION OF THE DRAWINGS

These and other objects and advantages and further description will now be discussed in connection with the drawings in which.

DESCRIPTION OF THE PREFERRED EMBODIMENTS

Figure 11:
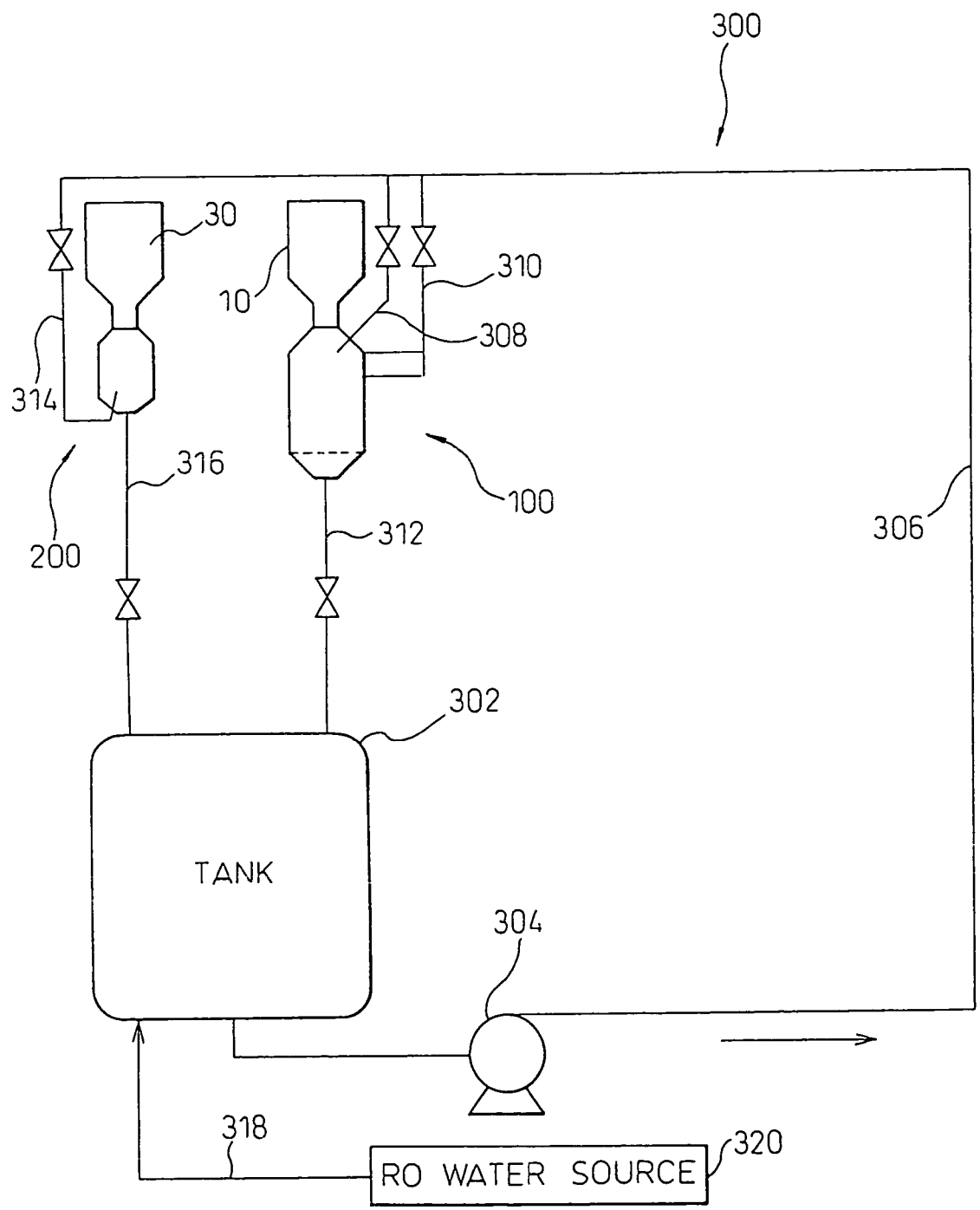
FIG. 11 is an apparatus for preparing a fluid for a medical procedure according to the invention.

FIG. 11 shows an example of an apparatus for preparing a fluid for a medical procedure according an embodiment of the invention. The apparatus 300 includes a tank 302 for containing the fluid, first and second openers 100 and 200 for opening bottles or first and second vessels 10 and 30 which contain medicament in the forms of powder and liquid, respectively. A pump 304 is provided for circulation of the liquid within the apparatus 300. RO water is supplied to the tank 302 from a RO water source 320 through a supply conduit 318. The RO water contained in the tank 302 is then supplied to the first opener 100 through a main conduit 306 including the pump 304 and a branch conduit 308 connected between the main conduit 306 and the first opener 100. Likewise, the RO water is supplied to the second opener 200 through the main conduit 306 and a branch conduit 314 connected between the main conduit 306 and the second opener 200.

The first opener 100 opens the seal of the first vessel 10 to remove the medicament in the form of powder from the first vessel 10 and receives it. The medicament received by the first opener 100 is dissolved into the OR water supplied to the first opener 100. The liquid containing the dissolved medicament flows back to the tank 302 through a return conduit 312.

Likewise, the second opener 200 opens the seal of the second vessel 30 to remove the medicament in the form of liquid from the second vessel 30. The medicament from the second vessel 30 is mixed with the OR water supplied to the second opener 100, and the mixture flows back to the tank 302 through a return conduit 316.

With reference to FIGS. 1–7, the first opener 100 according to the embodiment of the invention will be described below.

The first opener 100 includes a housing defined by upper and lower housings 102 and 104 and a bottom 105 which are connected to each other by a clamp rings 108 and 110. The upper housing 102 defines an upper open end 102a for receiving a holder 106. The holder 106 is displaceable relative to and within the upper housing 102 in the vertical direction along the central axis "O" of the housing. The bottom 105 has an outlet 105a which is adapted for the connection with the conduit 312.

Figure 3:
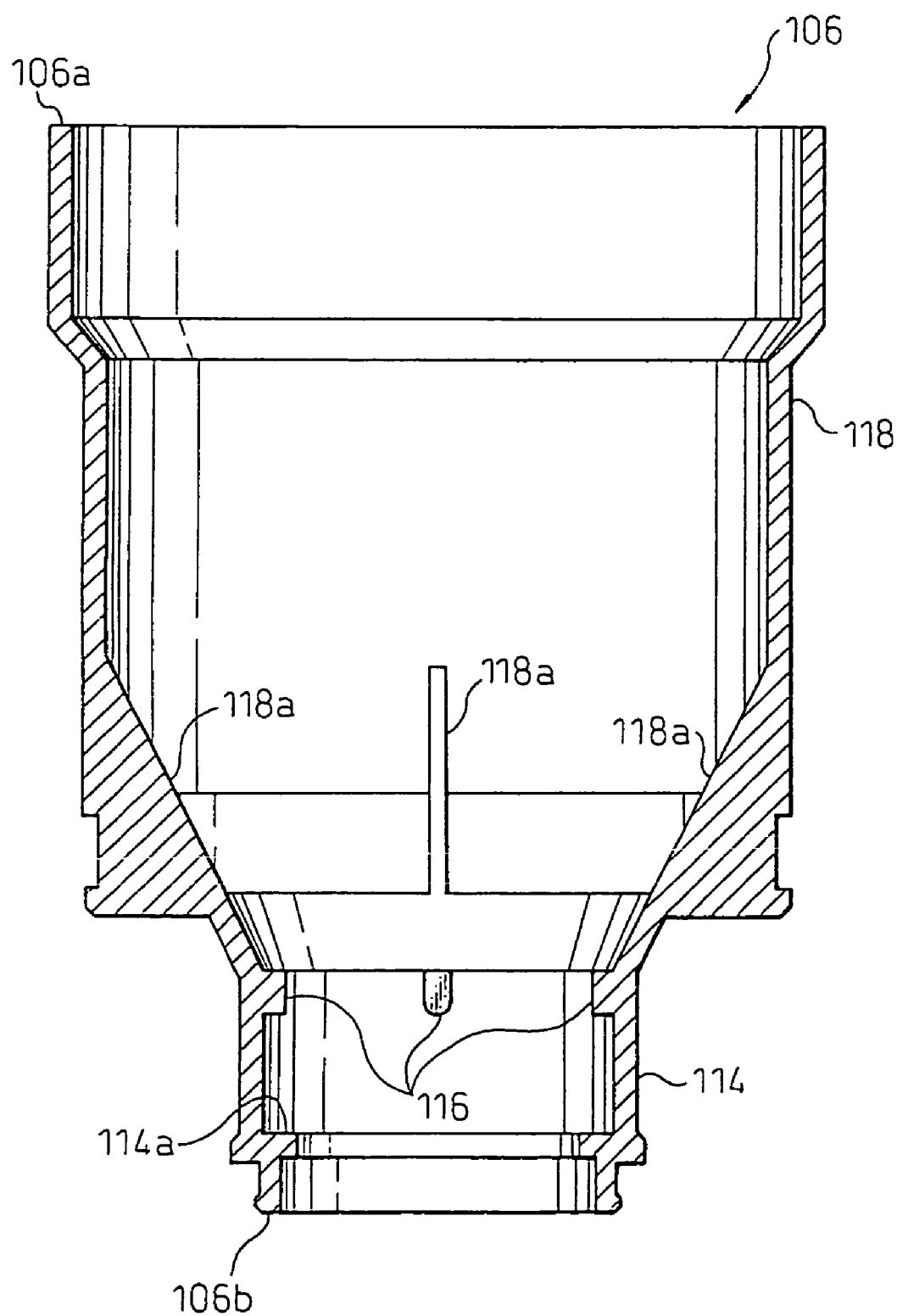
FIG. 3 is a vertical section of a holder according to the embodiment shown in FIG. 1.

With reference to FIG. 3, the holder 106 has a substantially cylindrical side wall 118 defining an upper open end 106a for receiving a fist vessel 10, as described hereinafter, and a neck 114 defining a lower opening end 106b. The neck 114 further defines a plurality of inwardly extending lugs 116 which are equally disposed at its upper end and an inwardly extending annular stop 114a adjacent to its lower end. The side wall 118 may have a plurality of inclined ribs 118a for aiding the insertion of the first vessel 10.

The first vessel 10 is adapted to contain solid medicament in the form of power or granular and has a bottom 12, a side wall 14 and a neck 16 which has a radius smaller than the side wall 14. The side wall 14 includes a cylindrical portion 14a and a truncated cone portion 14b which connects the end of the upper cylindrical portion 14a opposite to the bottom 12 to one end of the neck 16.

Figure 4:
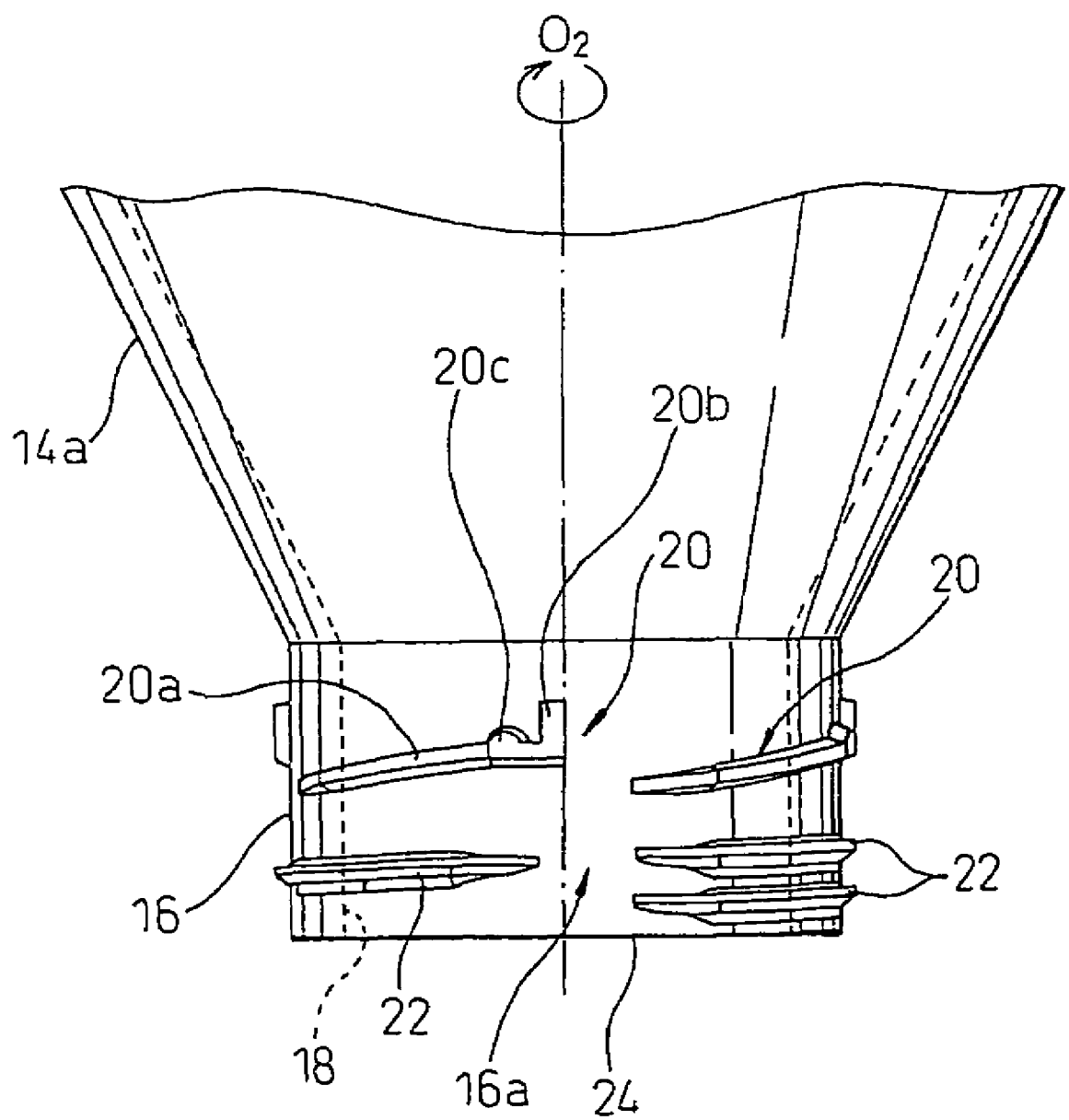
FIG. 4 is a partially enlarged side view of a vessel according to the embodiment shown in FIG. 1.

With reference to FIG. 4 the neck 16 includes a plurality of engagement portions 20 and screw portions 22. Each of the engagement portions includes a guide portion spirally extending along the outer surface of the neck 16, a stop portion 20b provided upper end of the spirally extending guide portion 20a and a protrusion 20c. The neck 16 further defines an opening 18 which is air-tightly sealed by a seal in the form of a membrane 24. Though the opening 18, a solid medicament in the form powder or granules is charged into and removed from the first vessel 10.

The engagement portions 20 are equally disposed on the outer surface of the neck 16 about the axis O2 of the first vessel 10 so that space 16a is provided between the stop 20b and the end of the guide 20a of the adjacent engagement portion 20. Likewise, the screw portions 22 are disposed on the outer surface of the neck 16 to provide the spaces 16a between the adjacent screws 22. The spaces 16a allow the passage of the protrusions 20c when the first vessel 10 is attached to the holder 112.

Figure 1:
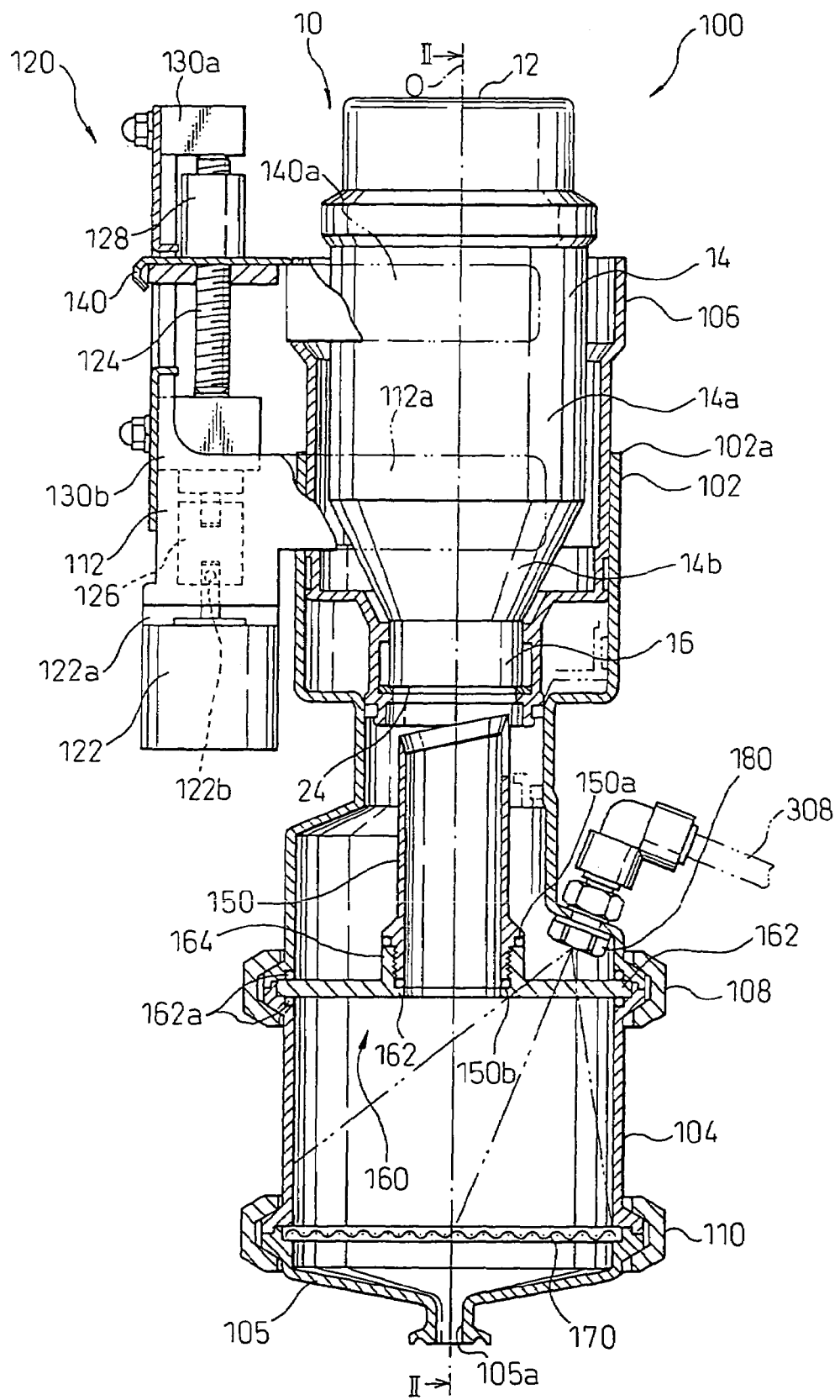
FIG. 1 is a vertical section of an embodiment of an opener according the invention.
Figure 2:
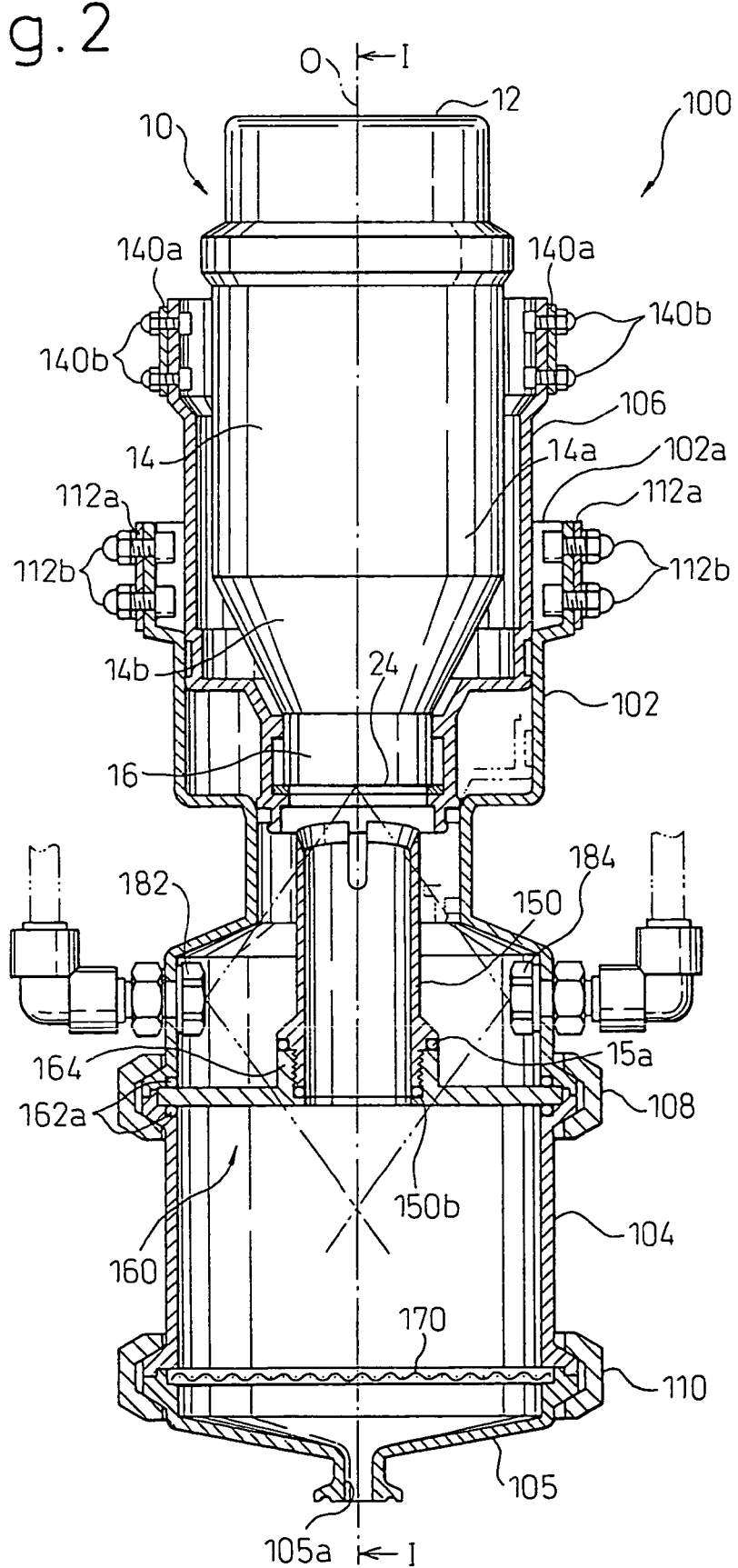
FIG. 2 is a vertical section of the opener along line I—I in FIG. 1.

FIGS. 1 and 2 show the first opener 100 with the first vessel 10 mounted thereto. The first opener 100 has a cutter 150 which is provided within the housing opposite to the opening 18 of the first vessel 10.

The upper hosing 102 of the first opener 100 is vertically supported by a stationary frame 112. The frame 112 has a pair of arms 112a which extend horizontally along the outer surface of the side wall upper housing 102 and are secured thereto by a plurality of screws 112b (FIG. 2).

The first opener 100 further includes a mechanism 120 for vertically moving the holder 106. The mechanism 120 includes an electric motor 122 attached to the frame 112 by a bracket 122a, and a vertically extending feed screw 124 supported by bearings 130a and 130b at the ends of the screw 124. At the lower end of the feed screw 124 is connected to the shaft 122b of the motor 122 by a coupling 126. A nut 128 which engages the feed screw 124 is mounted to a connection member 140. The connection member 140 has a pair of arms 140a which extend horizontally along the outer surface of the side wall of the cutter support 160 and are secured thereto by a plurality of screws 140b (FIG. 2).

With reference to FIGS. 5A to 5E, the configuration of the cutter 150 is described below.

The cutter 150 includes a substantially cylindrical cutter body 150 with a lower end defining a threaded portion 154, a flange 155 provided over the threaded portion 154, and an inclined upper end 156 defining an cutting edge. The cutter body 152 further includes a plurality of openings 152a (four openings 152a are shown in this embodiment) which define columns 152b supporting the upper portion of the cutter body 152.

Figure 5A:
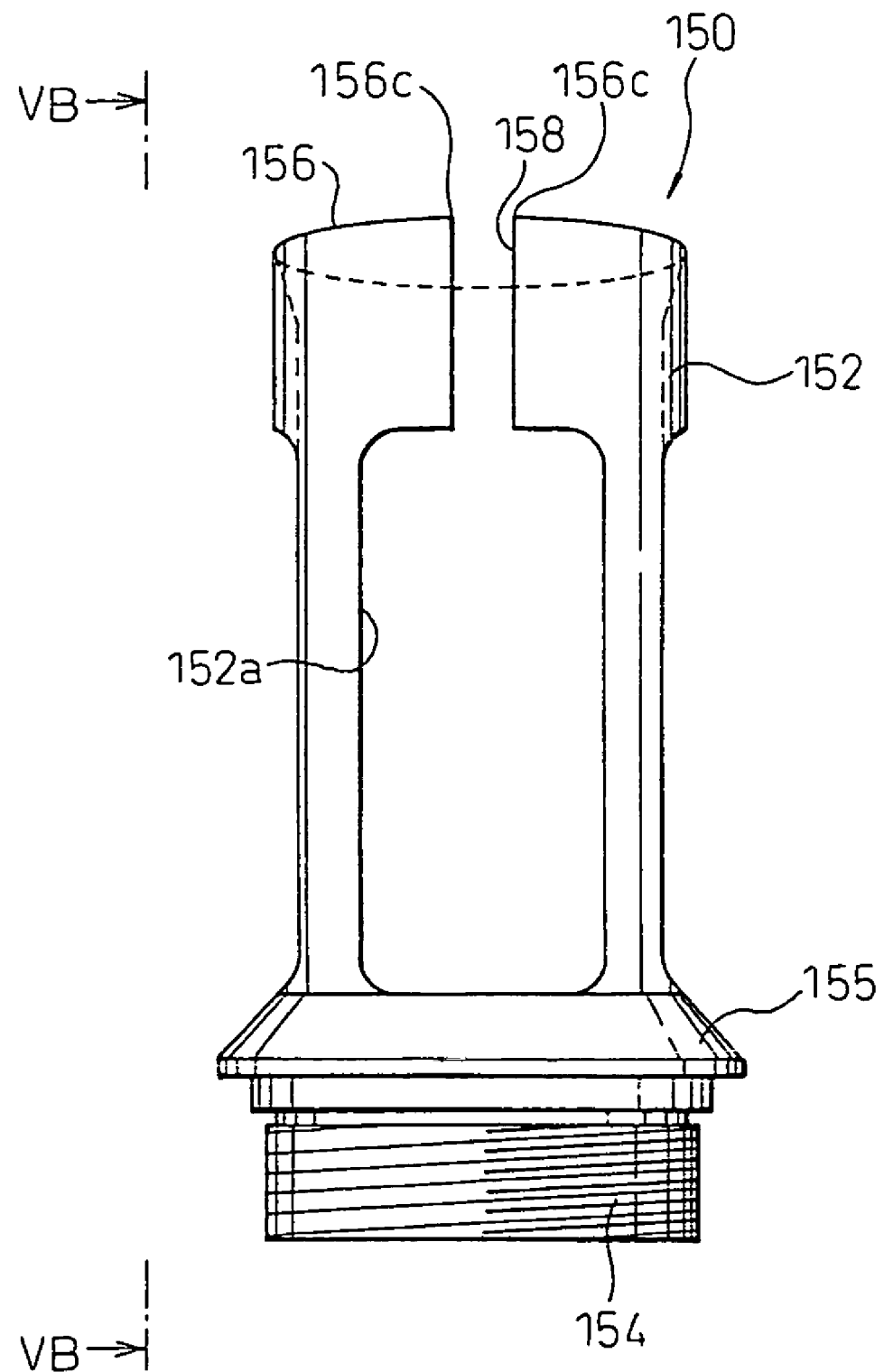
FIG. 5A is a side view of a cutter according to the embodiment shown in FIG. 1.
Figure 5B:
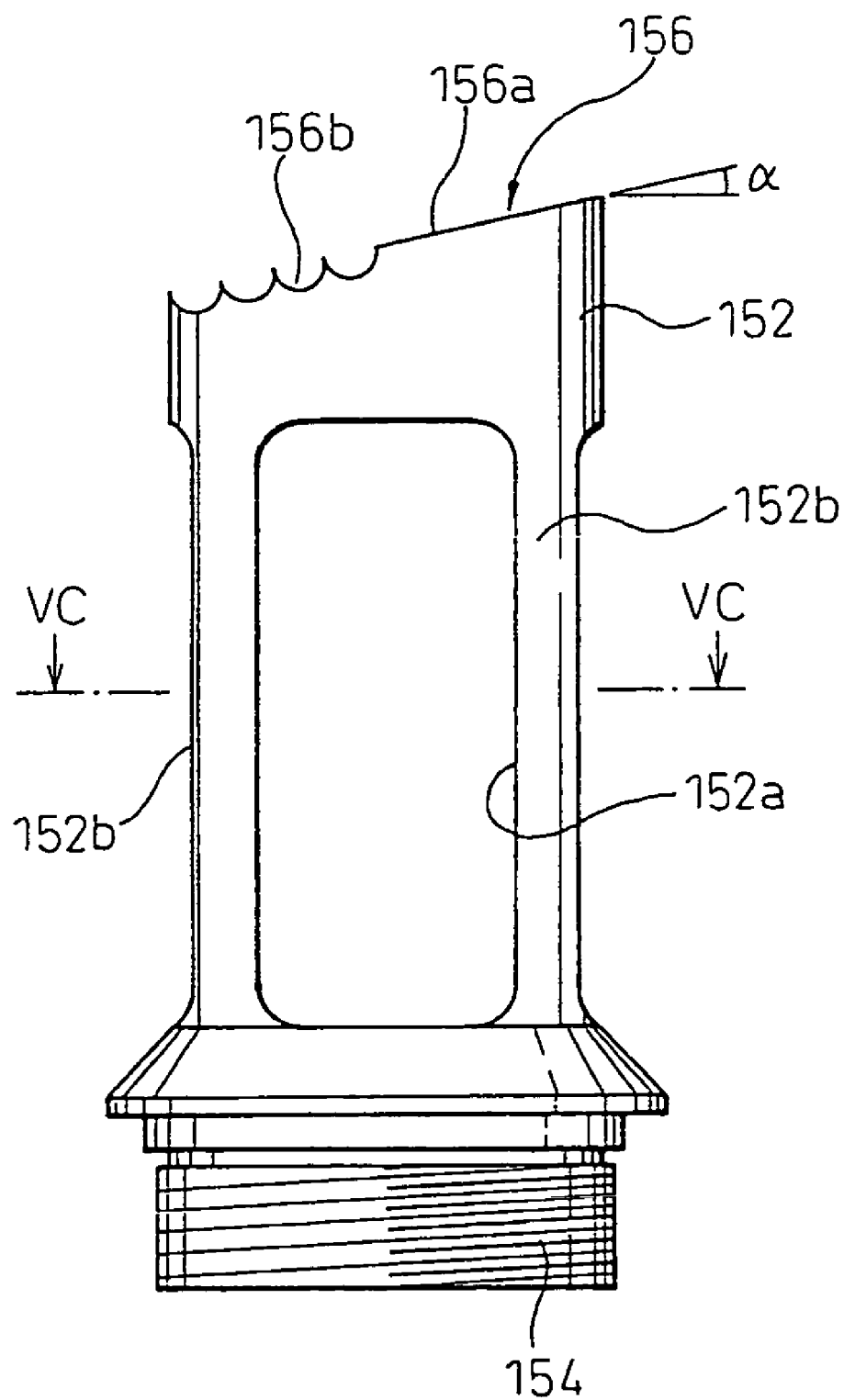
FIG. 5B is another side view of the cutter in the direction VB—VB in FIG. 5A.
Figure 5C:
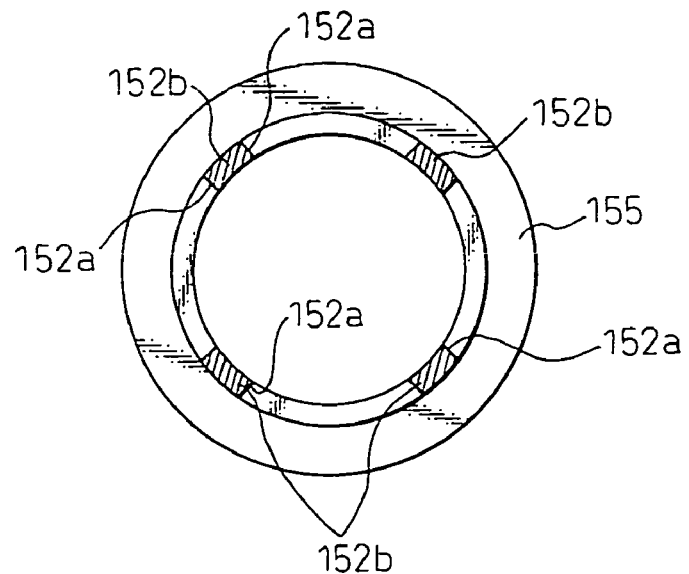
FIG. 5C is a horizontal section of the cutter along line VC—VC in FIG. 5A.
Figure 5D:
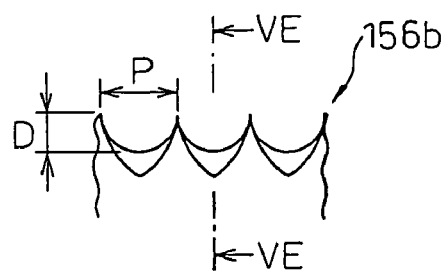
FIG. 5D is a partially enlarged section of the cutting edge of the cutter along line VD—VD in FIG. 5E.
Figure 5E:
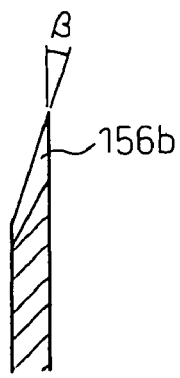
FIG. 5E is a partially enlarge side view of the cutting edge of the cutter.
Figure 6:
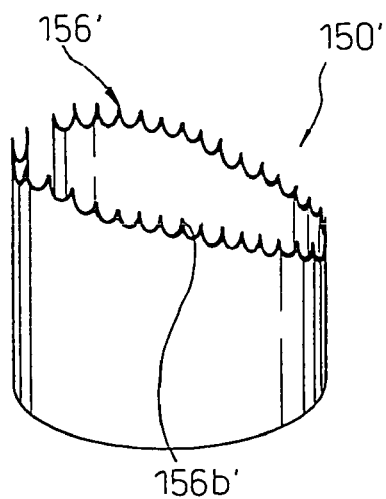
FIG. 6 is a perspective view of a cutter according to another embodiment of the invention.

The upper end 156 inclines from a plane perpendicular to the axis of the cutter body 152 by an angle α (FIG. 5B) of, preferably, 15–30 degrees. From the peak of the inclined end 156, a slit 158 vertically extends to one of the opening 152a. The inclined end 156 includes a plain cutting edge portion 156a which extend along upper half of the inclined end 156 and a serrated edge portion 156b provided on the lower half of the inclined end 156. FIG. 5D shows a portion of the serrated portion 156b, and FIG. 5E shows a partial side section of the serrated portion 156b along line VE—VE in FIG. 5D. The pitch "P" (see FIG. 5E), the distance between the peaks of the adjacent teeth of the serrated portion 156a, may be 1–5 mm, preferably 3 mm, and the depth "D" of the teeth may be 1–5 mm, preferably 3 mm. Further, the attack angle β may be 15–30 degrees, preferably 20 degrees. Further, the serrated portion may be provided all around the inclined end of the cutter body as shown in FIG. 6.

Figure 7:
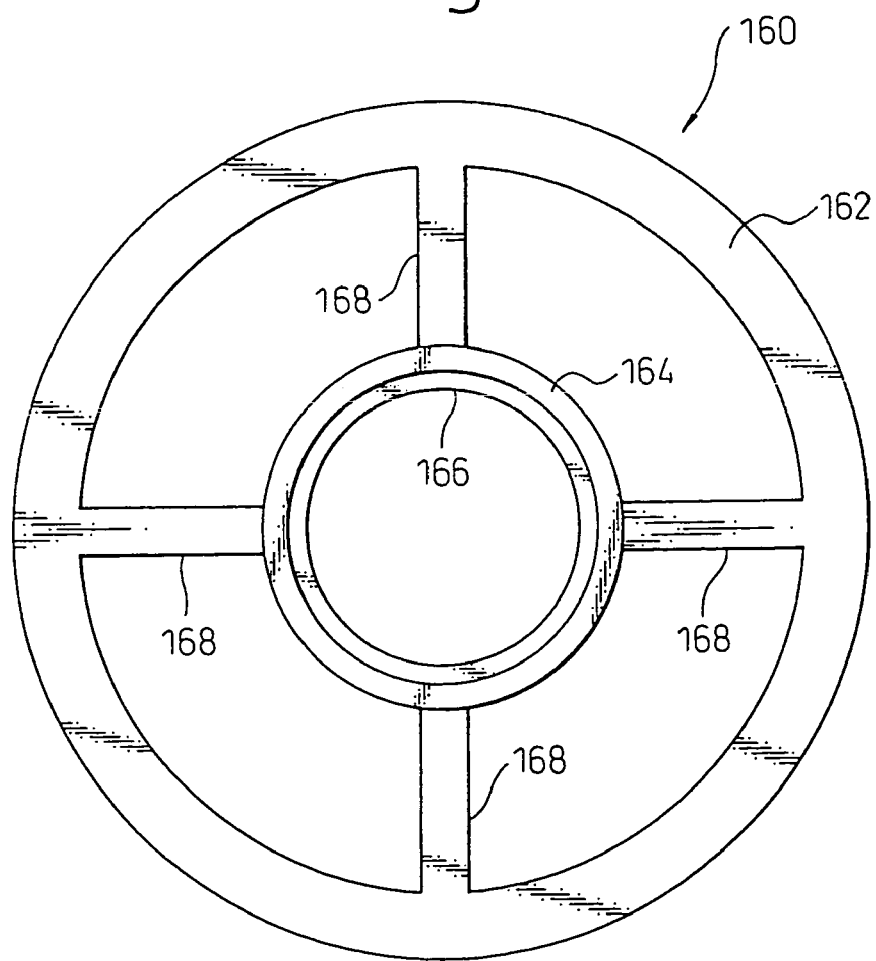
FIG. 7 is a cutter support according the embodiment shown in FIG. 1.

The cutter 150 is attached to and supported by an inner frame 160 which is clamped between the upper and lower housings 102 and 104. With reference to FIG. 7, the inner frame 160 includes a circular base 162 adapted to be clamped by the housings 102 and 104 with seal rings 162a provided therebetween (FIGS. 1 and 2), and a central mount 164 which is connected to the circular base 162 by radial spokes 168. The central mount 164 has a substantially cylindrical shape with a central bore including a threaded inner surface and a stop 162. The cutter 150 is attached to the central mount 164 through the engagement between the threaded portion 154 of the cutter 150 and the threaded inner surface of the central mount 164 with O-rings 150a and 150b clamped therebetween (FIGS. 1 and 2).

A receiving member 170, for receiving the solid medicament falling down from the first vessel 10 when the seal is broken by the first opener 100, is provided between the lower housing 104 and the bottom 105. The receiving member 170 includes a screen which can receive the medicament from the first vessel 10. The size of the powder of granules of sodium bicarbonate of 200 μm is generally used for preparing a fluid for dialysis treatment. Therefore, the mesh size of the screen is of at most 200 μm. On the other hand, a screen having a unnecessarily small mesh size, for example under 20 μm, inhibits the flow of the solution through the mesh, which results in increase in the pressure within the housing above the screen to break the seal of the first opener 100. The typical mesh size for the screen is of at least 20 μm, preferably 50–150 μm.

A water supply nozzle 180 is mounted to the housing of the first opener 100 and connected to the branch conduit 308. The water supply nozzle 180 is oriented to the receiving member 170 to direct the water in the form of a spray onto the medicament received on the receiving member 170.

The first opener 100 further includes a pair of washing nozzles 182 and 184 connected to a branch conduit 310 which is further connected to the main conduit 306 (FIG. 11). The washing nozzles 182 and 184 are horizontally oppositely oriented to the cutter 150 to direct the liquid from the tank 302 in the form of a spray for the purpose of washing inside of the housing of the first opener 100 and the cutter 150 after an operation of dissolving the medicament received on the receiving member 170 by spraying the RO water from the water supplying nozzle 180.

Figure 8:
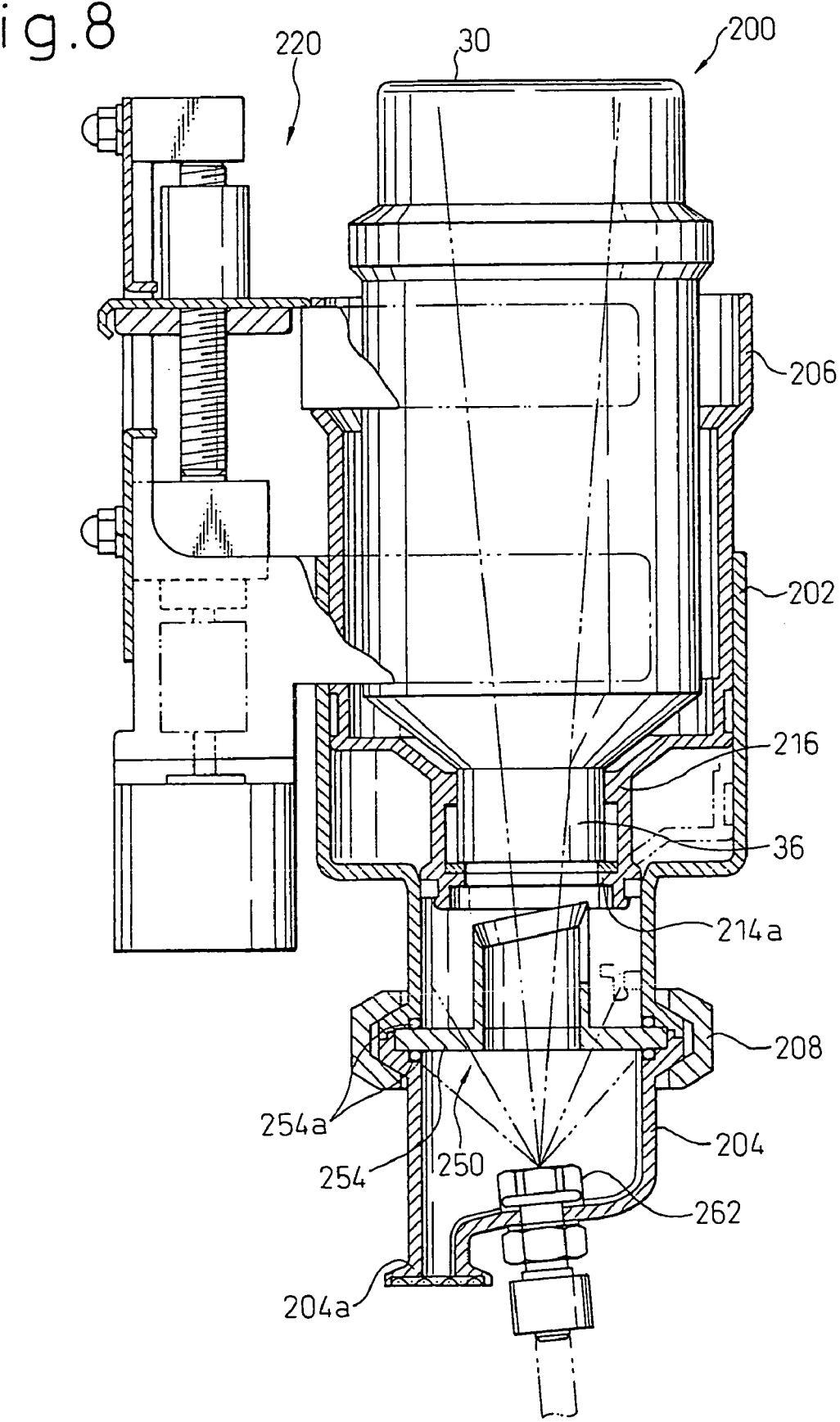
FIG. 8 is a vertical section of an opener according to another embodiment of the invention.
Figure 9A:
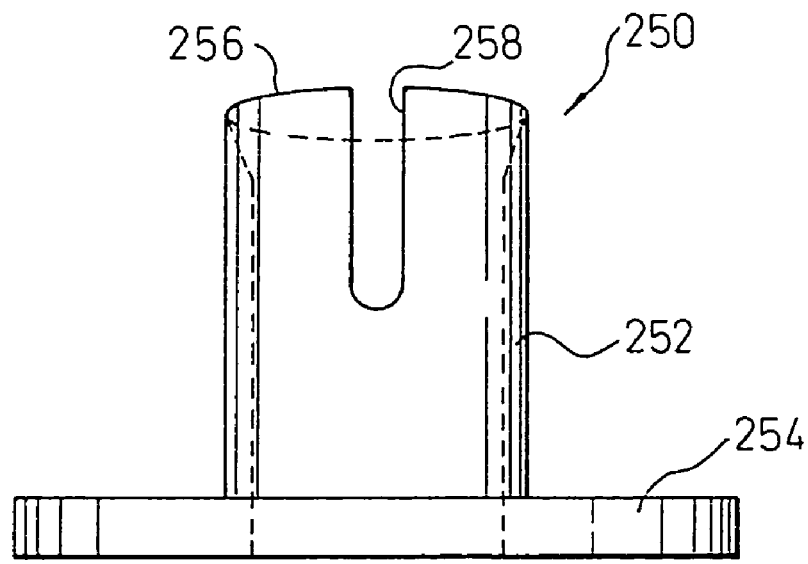
FIG. 9A is a side view of a cutter according to the embodiment shown in FIG. 8.
Figure 9B:
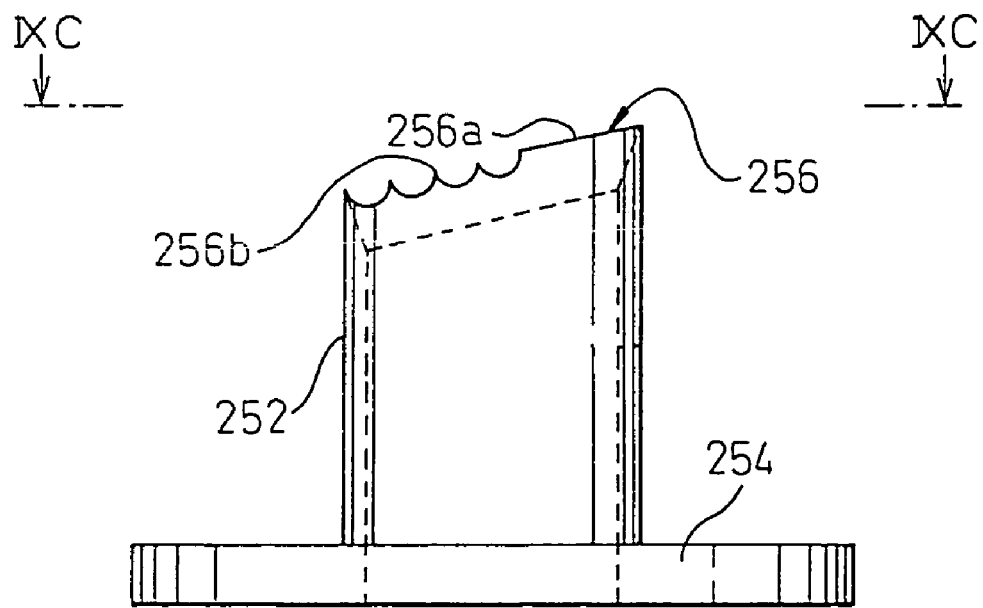
FIG. 9B is another side view of the cutter shown in FIG. 9A.
Figure 9C:
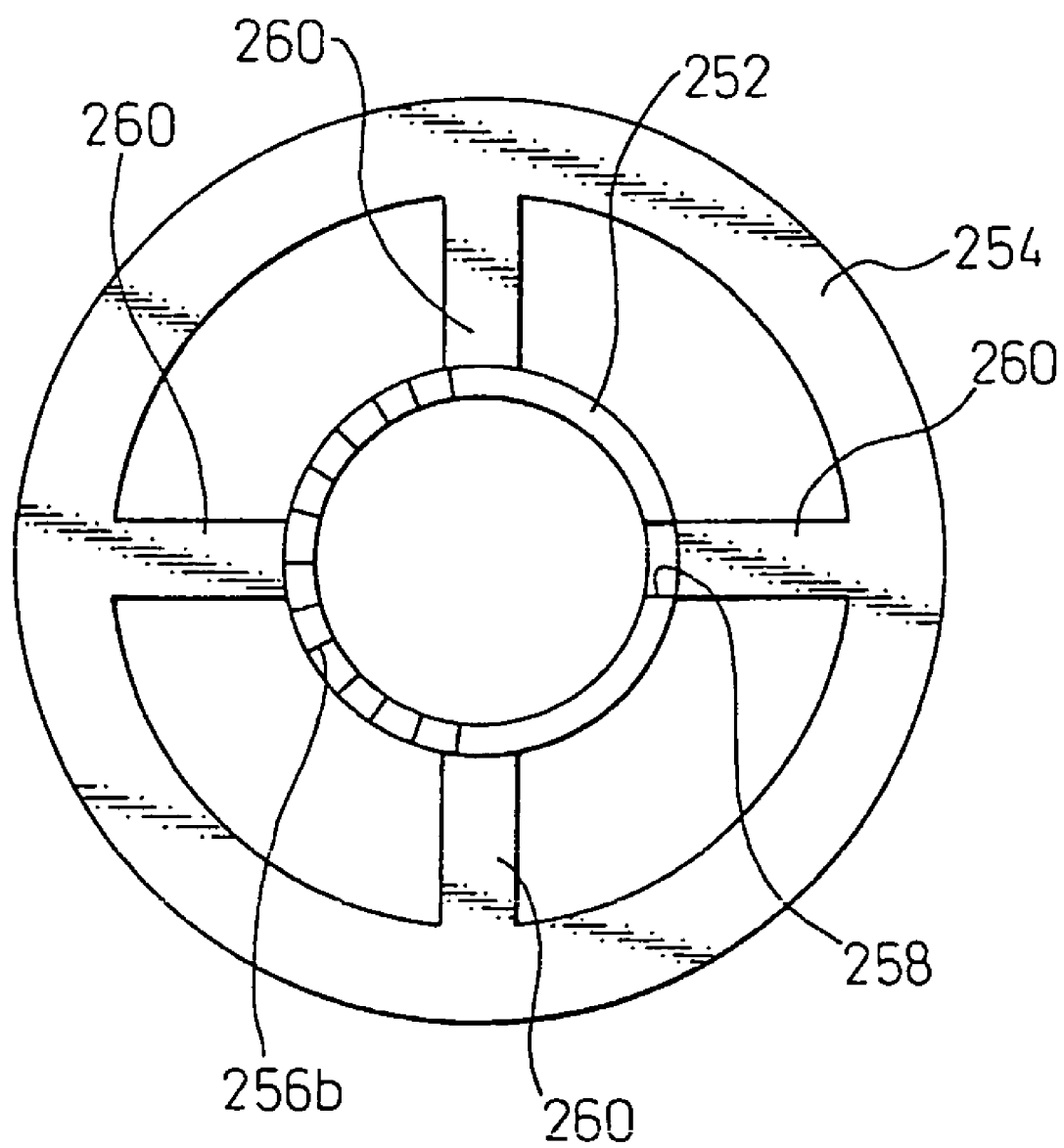
FIG. 9C is a plan view of the cutter viewed in the direction of IXC—IXC in FIG. 1A.

With reference to FIGS. 8–9C, the second opener 200 will be described below.

The second opener 200 is configured substantially the same as the first opener 100, except that the second opener 200 is adapted to open the seal of the second vessel 30 for containing a liquid medicament while the first opener 100 is adapted to open the first vessel 10 for containing a solid medicament in the form of power or granular.

The second opener 200 includes upper housing 202 and lower housing 204 which are connected to each other by a clamp ring 208 to define the housing of the second opener 200. The lower housing defines a bottom of the housing and an outlet 204a for connection with the return conduit 316 (FIG. 11).

The upper housing 202 vertically displaceablly receives a holder 206 for holding the second vessel 30. A mechanism 220, which is configured substantially the same as the mechanism 120 of the first opener 100, is provided for vertically moving the holder 206 relative to the upper housing 202.

A cutter 250 is provided within the housing opposite to the opening of the first vessel 30. The cutter 250 is formed substantially the same as the cutter 150 of the first opener 100, except that the cutter 250 of the second opener 200 is formed into one piece while the cutter 150 of the first opener 100 includes two pieces. The cutter 250 includes substantially a cylindrical cutter body 252 and a circular base portion 254. The cutter body 252 is disposed at the center of the circular base portion 254 and supported by radial spokes 260. The circular base portion 254 is adapted to be clamped by the housings 202 and 204 with seal rings provided therebetween (FIGS. 1 and 2), The cutter body 252 includes an inclined upper end 256 defining an cutting edge. The upper end 256 inclines from a plane perpendicular to the axis of the cutter body 252, the same as the cutter of the first opener 100.

From the peak of the inclined end 256, a slit 258 vertically extends into the cutter body 252. The inclined end 256 includes an plain cutting edge portion 256a which extend along upper half of the inclined end 256 and a serrated edge portion 256b provided on the lower half of the inclined end 256.

A water supplying nozzle 262 is attached to the bottom of the lower housing 204. The water supplying nozzle 262 is oriented substantially to the center of the cutter 250 to direct the water in the form of a spray to the inside of the second vessel 200 through the central bore of the cutter 250 for the purpose of flushing the inside of the second vessel.

The functional operation of the apparatus for preparing a fluid for a medical procedure of the invention will be described below.

First, the first and second vessels 10 and 30 are mounted to the first and second openers 100 and 200, respectively. The first and second vessels 10 and 30 are inverted after their caps (not shown) are removed. The necks 16 and 36 of the first and second vessels 10 and 30 are inserted into the bores defined by the necks 114 and 214 of the holders 106 and 206 of the first and second openers 100 and 200, respectively, so that the lugs 116 and 216 pass through the spaces 16a (only the space 16a of the first vessel 10 is shown in the drawings) provided on the outer surfaces of the necks 16 and 36. When the ends of the necks 16 and 36 abut the stops 114a and 214a of the holders 206 and 306, the first and second vessels 10 and 30 are rotated to engage the protrusions 20c (only the protrusions 20c of the first vessel 10 are shown in the drawings) provided on the outer surfaces of the necks 16 and 36 with the lugs 116 and 216. This secures the first and second vessels 10 and 30 to the holders 106 and 206 of the first and second openers 100 and 200.

After the first and second vessels 10 and 30 are mounted to the first and second openers 100 and 200, the contents of the first and second vessels 10 and 20 are removed. In the following description, the operation of removing the solid medicament contained within the first vessel will be described.

The mechanism 120 may be activated by an operator so that the nut 128, the connection member 140 and the holder 106 with the first vessel 10 secured to the holder 106 move downwardly. When the tips 156c of the cutting edge 156a of the cutter 150 contact the membrane 24 closing the opening 18 of the first vessel 10, the cutter 150 initiates cutting the membrane 24 in the opposite direction along the inner periphery of the opening 18 of the neck 16. Penetration of the inclined end 156 into the membrane 24 proceeds the cutting operation so that the membrane 24 is cut along the inner periphery of the opening 18, except for a portion which is located corresponding to the location of the slit 158. The serrated portion 156*b* aids the cutting performance when the cutting operation is advanced and the tension in the membrane is reduced.

Then, the mechanism 120 moves the nut 128, the connection member 140, the holder 106 and the holder 106 upwardly from the cutter 150. Moving the vessel 10 from the cutter 150 makes the solid medicament within the first vessel 10 to fall down onto the receiving member 170. At this time, the portion of the membrane 24 which has not been cut by the cutter 150 due to the slit 158 keeps the membrane 24 connected to the neck 16. The water is directed to the solid medicament on the receiving member 170 through nozzle 180 to dissolve the solid medicament into the sprayed water. The solution flows back to the tank 302 through the outlet 105*a* and the conduit 312. The tank 302 must have a volume at least the volume of the first opener 100 to receive all of the solution at once.

After the solid medicament is completely solved, the water supply through the nozzle 180 is ended and the washing nozzles 182 and 184 start to spray water to clean the inside of the housing 102, 104 and 105 and the cutter 150. In particular, the openings 152*a* of the cutter 150 allow the sprayed water to access the inside of the hollow cutter 150 sufficiently.

The second opener 200 functions substantially the same as the first opener 100 except that, while the first vessel 10 contains a solid medicament, the second vessel 30 mounted to the second opener 200 contains a liquid medicament so that the dissolving operation of the content of the vessel is not required. Thus, unsealing the membrane attached to the opening of the second vessel 30 removes the liquid medicament from the second vessel 30 so that the liquid medicament flows to the tank 302 through the outlet 204*a* of the second opener 200 without any operation. After completion of the evacuation of the second vessel 30, the water supplying nozzle 262 sprays water toward the inside of the second vessel through the central bore of the cutter 250 to clean the insides of housing 202 and 204, the vessel 30 and the cutter 250.

Figure 10:
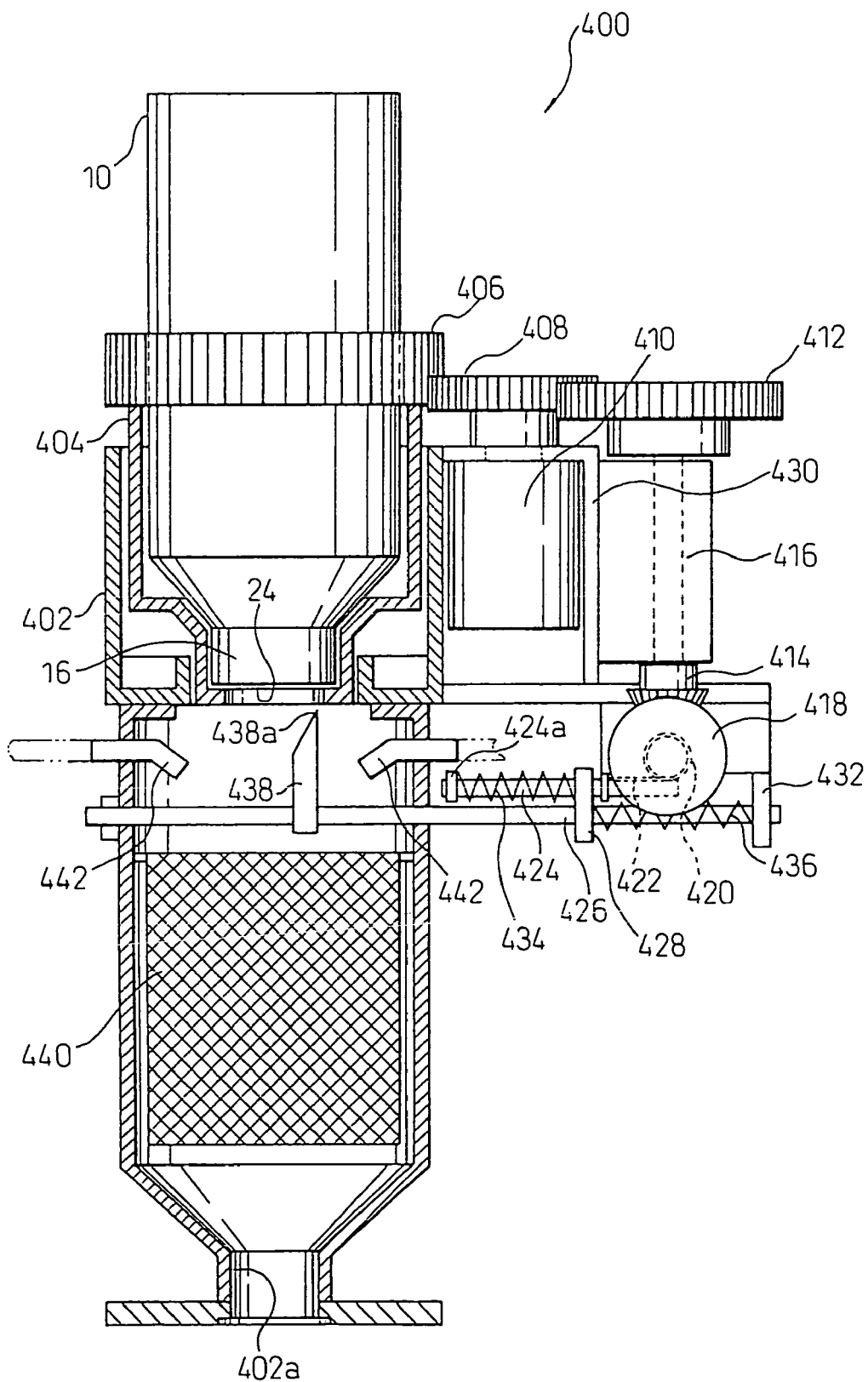
FIG. 10 is an opener according to another embodiment of the invention.

With reference to FIG. 10, an opener according to another embodiment of the invention will described below.

The opener 400 includes a housing 402 and a holder 404 to which the vessel 10 is mounted, same as the above-described embodiment. Although it is not shown in FIG. 10, the opener 400 also includes a mechanism, substantially the same as the mechanisms 120 and 240.

The holder 404 includes a first plain gear wheel 406 attached to the top of the holder 404. The first gear wheel 406 engages a drive gear wheel 408 attached to a shaft of an electric motor 410. The electric motor 410 is securely mounted to a frame 430. The rotation of the drive gear wheel 408 rotates the holder 404 through the engagement between the drive gear wheel 408 and the first gear wheel 406.

The drive gear wheel 408 also engages a second plain gear wheel 412. The second plain gear wheel 412 is connected to a bevel gear 414 by a shaft 416 to rotate therewith. The bevel gear 414 engages a second bevel gear 418. A pinion gear 420 is coaxially connected to the second bevel gear 418 to rotate therewith. The pinion gear 420 engages a rack 422 provided on a drive bar 424 which has a stop ring 424*a* at the end opposite to the rack 422.

Provided beneath the drive bar 424 is a driven bar 426 which horizontally extends through the housing 402. The driven bar 426 is displaceablely supported by a bracket 432 at one end, and the housing 492 at the other end. The bracket 432 is connected to the frame 430. A piece 428 is secured to the driven bar 428 to move therewith. The piece 428 has an aperture (not shown in FIG. 10) through which the drive bar 424 extends. Provided on the drive bar between the stop ring 424*a* and the piece 428 is a coil spring 434. Likewise, a coil spring 436 is provided on the driven bar 426 between the piece 428 and the bracket 432.

Provided on the driven bar 426 is a knife 438 which has a cutting edge 438*a* facing the membrane 24 sealingly closing the opening of the first vessel 10. A receiving member 440 in the form of a basket, which includes a screen or mesh provided in at least the bottom and a portion of the side wall, is provided beneath the knife 438. A pair of nozzles 442 is attached to direct water to the solid medicament received by the receiving member 440.

The functional operation of the opener 400 will be described below.

The first vessel 10 is mounted to the opener 400, as described above. After the first vessel 10 is mounted to the opener 400, the mechanism, substantially identical to the mechanism 120 and 220, may be activated by an operator to move the holder 404 downwardly with the first vessel 10 secured to the holder 404. The electric motor 410 is activated when the first gear wheel 406 engages the drive gear wheel 408. The activation of the electric motor 410 rotates the holder 404 through the engagement between the first gear wheel 406 and the drive gear wheel 408. Further, the activation of the electric motor 410 moves the drive bar 424 to the right in FIG. 10 through the gear train of the drive gear wheel 408, the second gear wheel 412, shaft 416, bevel gears 414 and 418, the pinion 420 and the rack 422. When the cutting edge 438*a* of the knife 438 contacts the membrane 24 closing the opening the first vessel 10, the cutting edge 438*a* of the knife 438 is substantially at the inside of the opening of the first vessel 10. The rotation of the holder 404 with the first vessel 10 secured to the holder 404 cuts the membrane 24 along the inner periphery of the opening of the first vessel 10.

The activation of the electric motor 410 is continued until the membrane 24 is cut along the inner periphery of the opening except for a portion to keep the membrane 24 cut by the knife 438 connected to the neck 16 by the portion.

When the opening of the first vessel 10 is unsealed, the solid medicament within the first vessel 10 falls down into the receiving member 440. The water is directed to the solid medicament in the receiving member 440 through nozzles 442 to solve the solid medicament into the sprayed water. The solution flows back to the tank 302 through the outlet 402*a* and the conduit 312.

It will also be understood by those skilled in the art that the forgoing description is a preferred embodiment of the disclosed device and that various changes and modifications may be made without departing from the spirit and scope of the invention.

The invention claimed is:

1. An apparatus for preparing a fluid for a medical procedure by mixing of at least one medicament in the form of powder with water, the medicament being held in a vessel which defines a bottom, a side wall, and a top opening which is closed by an membrane for sealing the inside of the vessel; the apparatus comprising:
   a source of water;
   an opener for opening the membrane of the vessel, the opener including a holder for vertically holding the vessel to downwardly orient the opening;
   a cutter, provided beneath the opening of the vessel held by the holder, for partially cutting the membrane along the periphery of the opening;

a mechanism for vertically moving the holder toward the cutter so that the cutting edge of the cutter pierces and partially separates the membrane from the periphery of the opening whereby the medicament in the vessel falls from the vessel;

a receiving member, in the form of a mesh provided beneath the cutter, for receiving all of the medicament from the vessel; and a nozzle for directing water from the source of water in the form of a spray to the medicament received by the receiving member to dissolve the medicament into the water directed to the medicament; and a tank connected to said receiving member for receiving and containing the substances dissolved in the sprayed water.

2. An apparatus according to claim 1, wherein the tank is adapted to receive the water from the water source; and the apparatus further comprising a circulating system for supplying the water from the tank to the nozzle.

3. An apparatus according to claim 1 wherein the opener further comprises a housing for enclosing the cutter and the receiving member, the holder being vertically displaceable relative to the housing, and the nozzle is attached to the housing to direct the water to the medicament received by the receiving member from outside of the housing.

4. An apparatus according to claim 1 wherein the mesh size of the receiving member is of at least 20 μm, preferably 50–150 μm.

5. An apparatus according to claim 1, wherein the mechanism comprises a feed screw vertically supported for rotation;
a motor, connected to one end of the feed screw, for rotating the screw;

a nut engaging the feed screw; and a member connected between the nut and the holder.

6. An apparatus according to claim 1, wherein the cutting edge includes a serrated portion provided along the inclined end.

7. An apparatus according to claim 6, wherein the serrated portion is partially provided along the inclined end of the cutter body.

8. An apparatus according to claim 7, wherein the serrated portion is disposed on the proximal half of the inclined end.

9. An apparatus according to claim 6, wherein the serrated portion is provided all around the inclined end of the cutter body.

10. An opener for opening the membrane of a vessel which contains at least one medicament in the form of powder and defines a bottom, a side wall, and a top opening which is closed by an membrane for sealing the inside of the vessel after the vessel receives a predetermined amount of the medicament, the opener comprising:

a holder for vertically holding the vessel to downwardly orient the opening;

a cutter, provided beneath the opening of the vessel held by the holder, for partially cutting the membrane along the periphery of the opening;

a mechanism for vertically moving the holder toward the cutter so that the cutting edge of the cutter pierces and partially separates the membrane from the periphery of the opening whereby the medicament in the vessel falls from the vessel;

a receiving member, in the form of a mesh provided beneath the cutter, for receiving all amount of the medicament from the vessel; and a nozzle for directing water in the form of a spray to the medicament received by the receiver member to dissolve the medicament into the water directed to the medicament.

11. An opener according to claim 10 further comprising a housing for enclosing the cutter and the receiving member, the holder being vertically displaceable relative to the housing, and the nozzle being attached to the housing to direct the water to the medicament received by the receiving member from outside of the housing.

12. An opener according to claim 10 wherein the mesh size of the receiving member is of at least 20 μm preferably 50–150 μm.

13. An opener according to claim 10, wherein the mechanism comprises a feed screw vertically supported for rotation;

a motor, connected to one end of the feed screw, for rotating the screw;

a nut engaging the feed screw; and a member connected between the nut and the holder.

14. An apparatus for preparing a fluid for a medical procedure by mixing of first and second medicaments with water, the first and second medicaments being held in first and second vessels each of which defines a bottom, a side wall, and a top opening which is closed by an membrane for sealing the inside of the vessel; the apparatus comprising:

a source of water;

a first opener for opening the membrane of the first vessel, the first opener including a holder for vertically holding the first vessel to downwardly orient the opening;

a cutter, provided beneath the opening of the first vessel held by the holder, for partially cutting the membrane along the periphery of the opening;

a mechanism for vertically moving the holder toward the cutter so that the cutting edge of the cutter pierces and partially separates the membrane from the periphery of the opening whereby the medicament in the vessel falls from the vessel;

a receiving member, in the form of a mesh provided beneath the cutter, for receiving all amount of the medicament from the first vessel; and a nozzle for directing water from the source of water in the form of a spray to the first medicament received by the receiving member to dissolve the first medicament into the water directed to the medicament;

a second opener for opening the membrane of the second vessel, the first opener including a holder for vertically holding the second vessel to downwardly orient the opening;

a cutter, provided beneath the opening of the second vessel held by the holder, for partially cutting the membrane along the periphery of the opening;

a mechanism for vertically moving the holder toward the cutter so that the cutting edge of the cutter pierces and partially separates the membrane from the periphery of the opening whereby the second medicament in the vessel falls from the vessel; and a nozzle for directing water from the source of water in the form of a spray to the inside of the second vessel; and a tank for receiving and containing the substances dissolved into the sprayed water.

* * * * *

UNITED STATES PATENT AND TRADEMARK OFFICE
CERTIFICATE OF CORRECTION

PATENT NO.        : 7,048,898 B1
APPLICATION NO. : 09/868580
DATED             : May 23, 2006
INVENTOR(S)       : Naohiko Moriyama et al.

It is certified that error appears in the above-identified patent and that said Letters Patent is hereby corrected as shown below:

Title Page, item (73) Assignees should read: Teijin Limited, Osaka (JP); Aksys Ltd., Lincolnshire, IL (US)

Signed and Sealed this

Twenty-second Day of August, 2006

JON W. DUDAS
*Director of the United States Patent and Trademark Office*